United States Patent [19]

Einlehner

[11] Patent Number: 4,633,701
[45] Date of Patent: Jan. 6, 1987

[54] ABRASION TESTING APPARATUS

[76] Inventor: Hans Einlehner, Industriestrasse 3a, 8901 Kissing, Fed. Rep. of Germany

[21] Appl. No.: 713,073

[22] Filed: Mar. 15, 1985

[30] Foreign Application Priority Data

Apr. 5, 1984 [DE] Fed. Rep. of Germany ... 8410643[U]

[51] Int. Cl.$^4$ .............................................. G01N 3/56
[52] U.S. Cl. ........................................ 73/7; 162/263
[58] Field of Search ................ 73/7, 8, 159; 162/263, 162/49, 198

[56] References Cited

U.S. PATENT DOCUMENTS

| 1,899,774 | 2/1933 | Rothchild et al. | 73/7 |
| 2,414,439 | 1/1947 | Brandon | 73/7 |
| 2,990,712 | 7/1961 | Weber | 73/7 |
| 3,388,584 | 6/1968 | Van de Velde | 73/7 |
| 3,554,007 | 1/1971 | Hu | 73/7 |
| 4,169,756 | 10/1979 | Chaudhuri | 73/7 X |
| 4,253,913 | 3/1981 | Chaudhuri | 73/7 X |

FOREIGN PATENT DOCUMENTS

| 2033592 | 1/1972 | Fed. Rep. of Germany. | |
| 563601 | 6/1977 | U.S.S.R. | 73/7 |

OTHER PUBLICATIONS

"Method of Investigating the Wear of Hord Tungsten Carbide Cobalt Alloys in a Liquid Nitrogen Medium"; Ind. Lob. (USA) vol. 38, No. 2; Feb. 1972; P. D. Shngrev et al.; pp. 302-304.
"Development of a Method for Evaluating the Relative Abrasiveness of a Corrugating Medium"; Project 2696-18; The Institute of Paper Chemistry; Report 1; 28 pages.
Pruefung Von Fuellstoffen und Pigmenten fuer Papier, Karton und Pappe and English translation thereof; pp. 1-6 in the German; Oct. 1975.
Description of Abrasion Tester Model AT 1000 by Ing. Hans Einlehner Pruefmaschinenbau, pp. 1-11; by Apr. 1984.
Wochenblatt fuer Papierfabrikation-pp. 295 and 296, vol. 9, 1981 in German.

Primary Examiner—Stewart J. Levy
Assistant Examiner—Tom Noland
Attorney, Agent, or Firm—Flynn, Thiel, Boutell & Tanis

[57] ABSTRACT

In an abrasion testing apparatus for determining abrasion in a screen caused by suction box coatings and the like in the cellulose and paper industry, a driving shaft (6) is provided on a drum (8), which drum is provided with suction device coatings at its circumference. The driving shaft is arranged vertically and the drum (8) is connected to the lowered end of the shaft and extends into the upper end of the tank (3) filled with filler suspension. The drum (8) is of hollow construction, has a plurality of openings (10) in its circumferential wall (8a) and is open at least at one end. A retaining and tensioning device for the portion of the screen (14) to be tested has two pairs of clamping bars (15a, 15b; 16a, 16b) arranged in the tank (3), each of which pairs is connected to a supporting rod (18, 19) extending into the open top of the tank (3), one of which supporting rods (18) is arranged to be stationary, while the other supporting rod (19) is arranged on a tensioning level (21) swingable about a vertical axis (V) and loaded by a predetermined force.

14 Claims, 3 Drawing Figures

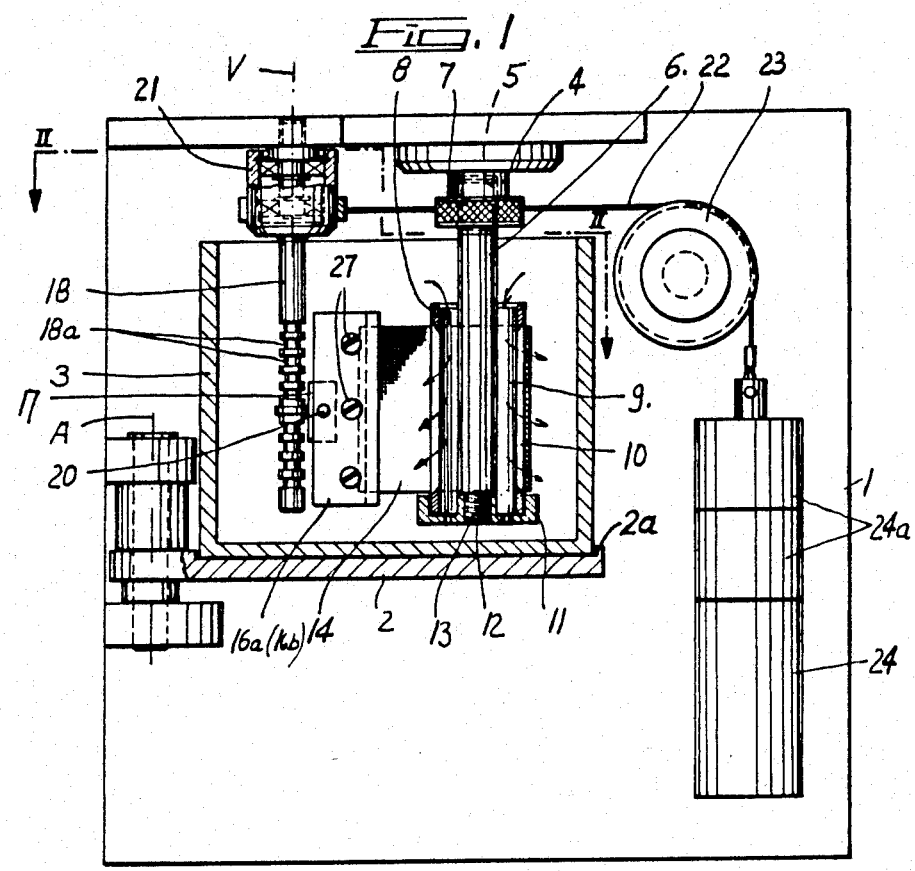
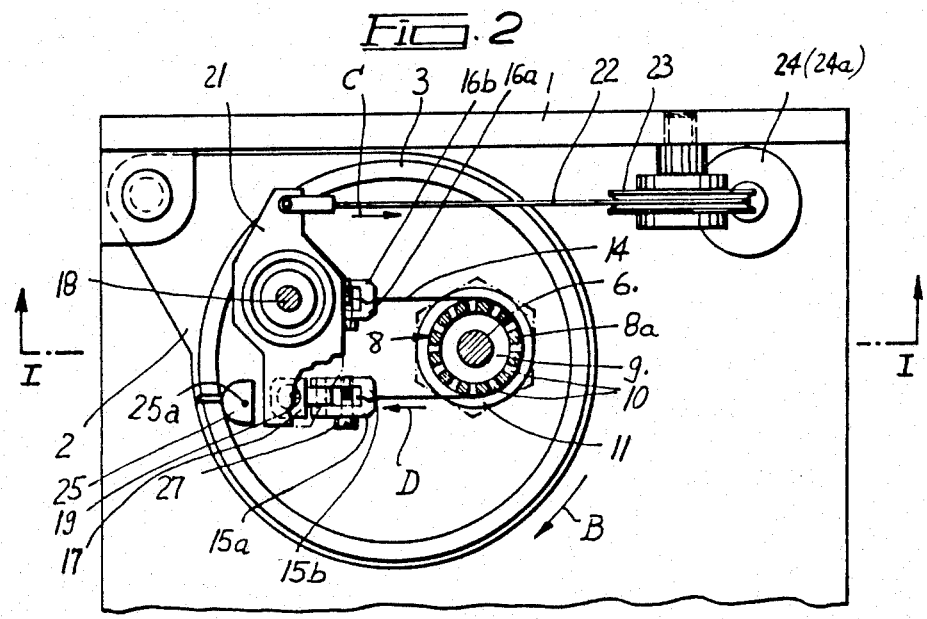
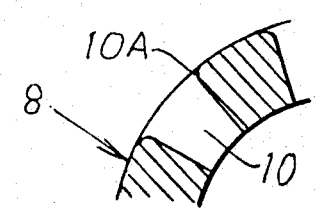

ABRASION TESTING APPARATUS

FIELD OF THE INVENTION

The invention relates to an abrasion testing apparatus for determining abrasion in a screen from suction box coatings and the like in the cellulose and paper industry. The apparatus includes a drum arranged in a tank containing a filler suspension, which drum is mounted on a driving shaft and on whose circumference suction device coatings are provided, and a substantially stationary retaining and tensioning device for a test piece formed by a portion of the screen, by means of which the test piece can be pressed against a part of the circumference of the drum.

BACKGROUND OF THE INVENTION

In the paper industry, fillers are presently suspended in water together with the fibrous materials and auxiliary substances. They come into contact with rotating and stationary parts or get between surfaces moving relative to one another on machine elements, such as, for example, suction device coatings and the screen of a paper machine.

In order to determine numerical data concerning the wearing effect of fillers in aqueous suspension in the cellulose and paper industry, as well as to determine wear in cellulose or pulp and paper machine screens and in the suction device coatings (ceramic, plastic and the like) employed therein, an abrasion testing apparatus has been developed (German Patent Specification No. 20 33 592) which is being used worldwide in the meantime under the name "AT 1000". The testing method special to this abrasion testing apparatus is defined in Leaflet V/27.5/75 issued by Verein der Zellstoff—und Papier-Chemiker und—Ingenieure (ZELLCHEMING) (Association of Cellulose and Paper Chemists and Engineers) and has thereby been acknowledged as obligatory by the relevant industry. In this abrasion testing apparatus, a standard test screen of phosphor bronze is employed as the test piece.

With the increased use of plastic screens instead of bronze screens in the cellulose and paper industry, the desire to use a standard plastic screen instead of the standard bronze screen has become ever stronger. Extensive investigations have shown, however, that when plastic screens are employed, no reproducible and significant test results can be obtained. It has been found, in fact, that certain fillers which showed a very slight abrasion effect with the use of bronze screens already led in part to complete destruction on plastic screens before the complete duration of the test. An additional aggravating factor as regards a possible choice of a standard plastic screen for determining abrasion is the fact that, depending on the quality of paper, not only are screens of varying fineness used as warp or weft runners, but also multi-layer screens have been tried out in practice. Finally, investigations have also shown that the surface roughness of a rotary ceramic body employed in the known testing apparatus exerts a great effect on the wear of the plastic screen. In order to get closer to conditions in practice, an abrasion testing apparatus has been developed experimentally (Wochenblatt der Papierfabrikation (Paper Manufacture Weekly) 9, 1981, page 295) which has essentially the structure mentioned at the beginning. In this apparatus, the driving shaft of the drum is arranged horizontally and eccentrically in a substantially cylindrical tank or container. The tank has an opening at the side. The retaining and tensioning device is provided in the region of this opening, this device having a chamber closed by a rubber diaphragm towards the circumference of the drum. By introducing compressed air into this chamber, the plastic screen held by the retaining and tensioning device can be pressed more or less strongly against the circumference of the drum. The tank has an inlet connection so that filler suspension can be fed into the crescent-shaped space between the drum and the wall of the tank. This filler suspension is intended to be entrained by the rotating drum, so that it gets between the surfaces in contact with each other, namely, between the suction device coatings arranged on the drum and the plastic screen pressed against the drum. This known abrasion testing apparatus, however, is comparatively costly to manufacture because of the complicated retaining and tensioning device. Moreover, a pump which keeps delivering the filler suspension back into the tank must be provided. Due to the horizontal arrangement of the driving shaft, considerable sealing problems moreover arise in those places where the driving shaft emerges from the tank and also where the tank has a lateral opening for the plastic screen. It is also not guaranteed that the filler emulsion will actually reach the zone between the suction device coatings and the plastic screen in sufficient quantity. Furthermore, the contact pressure of the plastic screen is not exactly reproducible and therefore, also, no reproducible test results can be obtained.

The problem underlying the invention is to provide an abrasion testing apparatus of the kind mentioned at the beginning which, together with simple design and long life, guarantees test conditions close to conditions obtained in practice and also enables acquisition of reproducible and comparable results.

SUMMARY OF THE INVENTION

According to the invention, this is achieved by arranging the driving shaft of the drum vertically and locating the drum concentrically at the lower end of the driving shaft, and support so that the drum extends into an upwardly open tank from above, and by making the drum of a hollow construction having a plurality of openings in the circumferential wall thereof and is open at least at its upper end, and with the retaining and tensioning device having two pairs of clamping bars arranged in the tank, each of which pairs is connected to a supporting rod which extends into the tank from above, one of which supporting rods is arranged to be stationary, while the other supporting rod is arranged on a tensioning lever swingable about a vertical axis and loaded by a predetermined force provided, for instance, by a weight or by spring tension.

The invention therefore starts from the idea of holding the test piece, in particular a plastic screen, at its two longitudinal edges by means of the clamping bars and looping it around about one half of the circumference of the drum after the fashion of a band brake. By causing a predetermined tensioning force, in particular a predetermined weight, to act on the tensioning lever, the screen can always be pressed against the drum with the same contact pressure, as a result of which reproducible and comparable test results are obtained. Since the suction device coatings arranged on the circumference of the drum always move in one and the same direction with respect to the stationary screen, this relative movement between the suction device coatings and the screen corresponds substantially to the conditions existing in practice. Added to this is the fact that during the rotation of the drum the filler suspension passes through the openings in the drum wall into the zone between the suction device coatings and the screen bearing against them. This guarantees that filler suspension is actually always present in sufficient quantity at the surfaces in contact with each other. Due to the vertical arrangement of the driving shaft and the suspended mounting of the drum on the shaft and also the holding of the screen by supporting rods extending into the tank from above, construction is decisively simplified. In fact, all sealing problems are disposed of. Moreover, there is no need for any circulating pump for the filler suspension to be present, because the filler suspension cannot escape from the tank and is constantly stirred up and thoroughly mixed by the rotation of the drum. Since the bearings for the driving shaft and also for the tensioning lever are disposed above and outside the tank, the filler suspension cannot reach these bearings, whereby problems of wear and corrosion are obviated.

Further advantageous developments of the invention will appear from the sub-claims.

BRIEF DESCRIPTION OF THE DRAWINGS

The invention is illustrated more fully in the following with reference to an embodiment shown in the drawing, in which:

FIG. 1 is a vertical section through the abrasion testing apparatus on the lines I—I in FIG. 2;

FIG. 2 is a horizontal section on the line II—II in FIG. 1; and

FIG. 3 is an enlarged detailed view of a fragmentary cross section of the circumferential wall of the drum used as a part of the abrasion testing apparatus.

DETAILED DESCRIPTION

On a frame 1 a table 2 is mounted to be swingable about a vertical axis A. A tank 3 can be arranged on the table 2. In order to avoid shifting of the tank 3 with respect to the table 2, the table 2 has a rim 2a embracing the bottom of the tank. If it is desired to remove the tank 3, it is raised slightly by a little more than the height of the rim 2a and the table 2 can then be swung forward and to the side in the direction B. The tank 3 can then be lowered.

In the top zone of the frame 1, an electric motor is arranged in the frame itself or in a housing (not shown) connected to the frame. The motor shaft 4 has at its lower end an internal thread 5 into which the vertical driving shaft 6 is screwed and is secured by the lock nut 7. On the lower end of the driving shaft 6 there is connected a drum 8, which shaft extends into the open top of the tank 3. The drum 8 preferably consists of the material of which the suction device coatings of paper and cellulose machines normally consist. This is preferably ceramic or else also plastic. If necessary, the suction device coatings may also be fixed to the circumference of the drum 8, which consists of a different material.

The drum 8 has a hollow space 9. The drum wall 8a is provided with a plurality of openings 10, preferably in the form of slits extending in the axial direction. If the drum 8 consists of ceramic, the slits are ground into the drum wall 8a by means of narrow grinding wheels. In order to create conditions as close as possible to those which exist in practice, the transitions of the slits 10 into the outer surface of the drum 8 are rounded off as at 10A in FIG. 3. If necessary, instead of the slits 10, bores may also be provided, but their transitions into the outer surface of the drum should likewise be rounded off.

As can further be seen from FIG. 1, the drum 8 is open at its upper end. For connecting the drum 8 to the driving shaft 6, a supporting plate 11 is arranged at the lower end of the drum and the drum 8 is fixedly connected to this plate, for example by cementing. The supporting plate 11 has a central internal thread 12 by means of which it is screwed onto an externally threaded end 13 provided on the lower end of the driving shaft 6.

In order to intensify the stirring action of the drum 8, a stirring device may be arranged at the lower end thereof. The stirring device is formed in the simplest way by providing the supporting plate 11 with suitable projections, for example as shown in chain-dotted lines in FIG. 2, by giving it a hexagonal form.

Furthermore, a retaining and tensioning device is provided for the test piece 14, in particular a plastic screen. In the first place, this retaining and tensioning device has two pairs of clamping bars 15a, 15b and 16a, 16b, respectively. Each of the two pairs consists of two clamping bars 15a, 15b or 16a, 16b which can be clamped together by means of screws 27. The transverse edges of the plastic screen 14 can be clamped in each case between two clamping bars 15a, 15b and 16a, 16b, respectively. Each of the pairs of clamping bars 15a, 15b and 16a, 16b, respectively, is connected via a supporting piece 17 to a supporting rod 18, 19. In order to ensure a uniform pressure of the plastic screen 14 against the circumference of the drum, each of the supporting pieces 17 is pivotally attached to the associated pair of clamping bars via a horizontal pivot pin 20. The supporting piece 17 has a vertical bore by means of which it can be suspended in one of the annular grooves 18a, 19a in the supporting rods 18, 19.

One supporting rod 18 having a vertical axis V is arranged to be stationary and serves at the same time for mounting the double-armed tensioning lever 21. The second supporting rod 19 is fixed to one arm of the tensioning lever 21. Both supporting rods 18, 19 extend into the open top of the tank 3. A traction cable 22 acts on the other arm of the tensioning lever 21, the cable being passed over a guide pulley 23. A basic weight 24 is attached to the traction cable 22. One or more supplementary weights 24a can be placed on top of the basic weight 24.

As can be seen from FIG. 2, the two supporting rods 18, 19 and, consequently, also the pairs of clamping bars 15a, 15b and 16a, 16b, respectively, are arranged at a distance apart which corresponds approximately to the diameter of the drum 8. In this way, the result is achieved that the screen to be tested embraces the drum over about 180° of its circumference.

Before the abrasion test is carried out, a rectangular piece of the plastic screen to be tested is weighed and then clamped securely between the pairs of clamping bars 15a, 15b and 16a, 16b outside the abrasion testing apparatus. By rotation of the locking member 25 about a vertical axis 25a, the retaining and tensioning device can be relieved of load, i.e. the action of the weights 24, 24a can be neutralized. The screen portion 14 is placed free from tension around the drum 8 and the two supporting pieces 17 are pushed onto the supporting rods 18, 19 from below and suspended in a suitable annular groove, only one groove 18a being illustrated in FIG. 1.

By rotation of the locking member 25 into the position shown in FIG. 2, the tensioning device is again put into operation. The weight 24 (24a) exerts on the tensioning lever 21 a force directed in the direction of the arrow C, whereby the screen 14 is tensioned in the direction D. By means of this tractive force of predetermined magnitude, the screen 14 is pressed against the drum 8 with a predetermined constant contact pressure. The tank 3 is filled with a filler suspension, for example a kaolin suspension, and is moved upwardly, so that the tank 3 adopts approximately the position shown in FIG. 1. The table 2 is then swung below the tank 3 and the latter is set down on the table. It then finally adopts the position shown in FIG. 1. The drum 8 is then driven for a predetermined time by means of the electric motor and the driving shaft 6. The screen 14 is thereafter removed from the abrasion testing apparatus in reverse sequence, carefully cleaned, dried and then weighed. The difference in the weights of the screen before and after the test represents the loss of weight of the screen through the testing process. The loss of weight is divided by the size of the abrasion area and the loss of weight per unit of area is thereby obtained. By measuring the decrease in thickness of the screen and observing the screen under a microscope, the test can be further supplemented.

During the rotation of the drum 8, the filler suspension contained in the interior of the drum is also entrained. As a result of this, there acts on the suspension present in the interior of the drum a centrifugal force which conveys the suspension to the outside through the openings 10. Consequently, suspension must flow in after this suspension through the top opening of the drum. Due to this conveying action of the drum, the suspension is kept in constant motion. The stirring up and thorough mixing of the suspension is also promoted by the supporting plate 11 designed as a stirring body. The constant thorough mixing of the suspension prevents settling and deposits of particles of material. This, in addition to the properly defined loading, is of decisive importance for exact and reproducible abrasion testing.

Not only plastic screens, but also metal screens, can be subjected to testing under conditions close to those arising in practice with the novel abrasion testing apparatus. If necessary, it is also conceivable to fix in the clamping jaws single monofilaments from which plastic screens are woven in order to be able to test the abrasion behaviour of these monofilaments even already before they are woven into a screen.

A table which can be raised and lowered and which is fixable in its top position could moreover be provided instead of a swing table for supporting the tank.

The embodiments of the invention in which an exclusive property or privilege is claimed are defined as follows:

1. In an abrasion testing apparatus for determining abrasion in a screen caused by suction box coatings and the like in the cellulose and paper industry, using a drum arranged in an open tank containing a filler suspension, said drum being mounted on a driving shaft, said drum having a circumference on which suction device coatings are provided, and with a substantially stationary retaining and tensioning means for holding a test piece, in the form of a portion of said screen, pressed against a part of the circumference of said drum, the improvement comprising wherein drive means are provided for rotatably driving said driving shaft, said driving shaft being arranged vertically and said drum being connected to the lower end of said driving shaft, which shaft extends into an upper end of said tank, said drum being of a hollow construction and has a plurality of openings in the circumferential wall thereof and is open at least at its upper end, and said retaining and tensioning means has two pairs of clamping bars arranged in said tank, each of which pairs is connected to a supporting rod extending into said open top of said tank, one of which supporting rods is arranged to be stationary, while the other supporting rod is arranged on a tensioning lever swingable about a vertical axis and loaded by a predetermined force.

2. The apparatus according to claim 1, wherein said supporting rods and said pairs of clamping bars are arranged side by side on one side of said drum at a distance apart which corresponds approximately to the diameter of said drum, so that said portion of said screen to be tested embraces said drum over about 180° of its circumference.

3. The apparatus according to claim 1, wherein each pair of clamping bars is connected via a supporting piece to an associated supporting rod, said supporting piece in turn being pivotally attached to said pair of clamping bars for movement about a horizontal pivot pin.

4. The apparatus according to claim 1, wherein said openings in said circumferential wall are slits which extend parallel to an axis of rotation of said driven shaft.

5. The apparatus according to claim 4, wherein each of said slits have opposed wall surfaces, wherein transition edges are defined at locations whereat said transition edges meet said wall surfaces, and wherein said transition edges are rounded off.

6. The apparatus according to claim 1, wherein the entire drum consists of the material of said suction device coatings.

7. The apparatus according to claim 6, wherein said drum consists of ceramic.

8. The apparatus according to claim 1, wherein said drum is open at its upper end.

9. The apparatus according to claim 8, wherein said drum is substantially closed at its lower end.

10. The apparatus according to claim 1, wherein a stirring device is arranged at the lower end of said drum.

11. The apparatus according to claim 10, wherein said lower end of said drum is connected to a supporting plate having a central internal thread which can be screwed onto an externally threaded end provided at said lower end of said driving shaft.

12. The apparatus according to claim 1, wherein a traction cable acts on said tensioning lever, said cable being passed over a guide pulley to a basic weight on top of which one or more supplementary weights can be placed to define said predetermined force.

13. The apparatus according to claim 1, wherein said tank is arranged on a table which can be swung about said vertical axis.

14. The apparatus according to claim 1, wherein said tank is arranged on a table which can be raised and lowered and is fixable in its top position.

* * * * *